US00PP17963P2

(12) United States Plant Patent
Westhoff

(10) Patent No.: US PP17,963 P2
(45) Date of Patent: Aug. 28, 2007

(54) ***LOBELIA* PLANT NAMED 'WESPINSTAR'**

(50) Latin Name: *Lobelia erinus*
Varietal Denomination: Wespinstar

(75) Inventor: Heinrich Westhoff, Südlohn (DE)

(73) Assignee: J. + H. Westhoff Interpel, Südlohn (DE)

( * ) Notice: Subject to any disclaimer, the term of this patent is extended or adjusted under 35 U.S.C. 154(b) by 0 days.

(21) Appl. No.: 11/358,892

(22) Filed: Feb. 17, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Lobelia* plant named 'Wespinstar', characterized by its cascading plant habit; vigorous growth habit; freely branching habit with short internodes; dense and bushy plant form; continuously and freely flowering habit; and light purple-colored flowers.

1 Drawing Sheet

Botanical designation: *Lobelia erinus.*
Cultivar denomination: 'Wespinstar'.

BACKGROUND OF THE INVENTION

The present Invention relates to a new and distinct cultivar of *Lobelia* plant, botanically known as *Lobelia erinus,* and hereinafter referred to by the name 'Wespinstar'.

The new *Lobelia* is a product of a planned breeding program conducted by the Inventor in Südlohn, Germany. The objective of the breeding program was to develop new vigorous *Lobelia* cultivars with unique flower colors.

The new *Lobelia* originated from a cross-pollination made by the Inventor in 2002 of a proprietary selection of *Lobelia erinus* identified as code number 02P616, not patented, as the female, or seed, parent with a proprietary selection of *Lobelia erinus* identified as code number 02P725, not patented, as the male, or pollen, parent. The new *Lobelia* was discovered and selected by the Inventor from within the resultant progeny from the above-mentioned cross-pollination in a controlled environment in Südlohn, Germany in 2002.

Asexual reproduction since 2003 of the new cultivar by terminal cuttings in a controlled environment in Südlohn, Germany, has shown that the unique features of this new *Lobelia* are stable and reproduced true to type in successive generations.

SUMMARY OF THE INVENTION

The following traits have been repeatedly observed and are determined to be the unique characteristics of 'Wespinstar'. These characteristics in combination distinguish 'Wespinstar' as a new and distinct cultivar:

1. Cascading plant habit.
2. Vigorous growth habit.
3. Freely branching habit with short internodes; dense and bushy plant form.
4. Continuously and freely flowering habit.
5. Light purple-colored flowers.

Plants of the cultivar Wescaosu can be compared to plants of the female parent selection. In side-by-side comparisons conducted in Südlohn, Germany, plants of the new *Lobelia* differed from plants of the female parent selection in the following characteristics:

1. Plants of the new *Lobelia* were more compact than plants of the female parent selection.
2. Plants of the new *Lobelia* were denser than plant plants of the female parent selection.
3. Plants of the new *Lobelia* and the female parent selection differed in flower color as plants of the female parent selection had more intense purple-colored flowers.

Plants of the cultivar Wescaosu can be compared to plants of the male parent selection. In side-by-side comparisons conducted in Südlohn, Germany, plants of the new *Lobelia* differed from plants of the male parent selection in the following characteristics:

1. Plants of the new *Lobelia* had smaller flowers than plants of the male parent selection.
2. Plants of the new *Lobelia* and the male parent selection differed in flower color as plants of the male parent selection had light lilac-colored flowers.

Plants of the new *Lobelia* can be compared to plants of the *Lobelia* cultivar Weslolav, disclosed in U.S. Plant Pat. No. 15,434. In side-by-side comparisons conducted in Südlohn, Germany, plants of the new *Lobelia* differed from plants of the cultivar Weslolav in the following characteristics:

1. Plants of the new *Lobelia* had longer lateral branches than plants of the cultivar Weslolav.
2. Plants of the new *Lobelia* had smaller flower buds than plants of the cultivar Weslolav.
3. Plants of the new *Lobelia* and the cultivar Weslolav differed in flower color.

Plants of the cultivar Wespinstar can also be compared to the cultivar Weslowei, disclosed in U.S. Plant Pat. No. 12,708. However in side-by-side comparisons conducted in Südlohn, Germany, plants of the cultivar Wespinstar and the cultivar Weslowei differed in the following characteristics:

1. Plants of the new *Lobelia* had longer lateral branches than plants of the cultivar Weslowei.
2. Plants of the new *Lobelia* had smaller flower buds and sepals than plants of the cultivar Weslowei.
3. Plants of the new *Lobelia* and the cultivar Weslowei differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description, which accurately describe the actual colors of the new *Lobelia*.

The photograph at the top of the sheet comprises a side perspective view of a typical plant of 'Wespinstar' grown in a hanging basket container.

The photograph at the bottom of the sheet comprises a close-up view of a typical individual flower of 'Wespinstar'.

DETAILED BOTANICAL DESCRIPTION

Plants of the cultivar Wespinstar have not been observed under all possible environmental conditions. The phenotype may vary somewhat with variations in environment such as temperature and light intensity without, however, any variance in genotype.

In the following description, color references are made to The Royal Horticultural Society Colour Chart, 2001 Edition, except where general terms of ordinary dictionary significance are used. Plants used for the aforementioned photographs and following description were grown in a glass-covered greenhouse and conditions that closely approximate commercial production conditions during the spring and summer in Südlohn, Germany. Plants were grown as one plant per 12-cm container or three plants per 25-cm hanging basket container. During the production of the plants, day temperatures ranged from 20° C. to 25° C. and night temperatures ranged from 16° C. to 18° C. Plants were pinched one time. Plants were about 22 weeks from planting when the photographs and description were taken.

Botanical classification: *Lobelia erinus* cultivar Wespinstar.

Parentage:

*Female parent.*—Proprietary selection of *Lobelia erinus* identified as code number 02P616, not patented.

*Male parent.*—Proprietary selection of *Lobelia erinus* identified as code number 02P725, not patented.

Propagation:

*Type cutting.*—Terminal vegetative cuttings.

*Time to initiate roots.*—About 14 to 18 days at 18° C. to 20° C.

*Time to produce a rooted young plant.*—About 21 to 24 days at 18° C. to 20° C.

*Root description.*—Fine, fibrous.

*Rooting habit.*—Freely branching.

Plant description:

*Plant form/habit.*—Cascading flowering plants with light purple-colored flowers. Lateral shoots outwardly spreading; plants uniform with dense foliage. Freely branching with lateral branches forming at every node; dense and bushy plant habit. Pinching plants enhances branching. Moderately vigorous growth habit.

*Usage.*—Appropriate for hanging baskets, window boxes and patio containers.

*Plant height* (*soil level to top of plant plane*).—About 12 cm to 20 cm.

*Plant length* (*soil level to lateral branches apices*).—About 40 cm to 50 cm.

*Branch description.*—Primary branch length: About 37 cm. Primary branch diameter: About 2.3 mm. Secondary branch length: About 19.8 cm. Secondary branch diameter: About 1.2 mm. Internode length: About 1.4 cm. Texture: Sparsely pubescent to glabrous. Color: 137A to 137B.

*Foliage description.*—Arrangement: Alternate, simple; sessile. Basal leaves: Length: About 5.1 cm. Width: About 1.8 cm. Shape: Oblanceolate. Apex: Emarginate. Base: Attenuate. Margin: Nearly entire with occasional indentations. Mid-plant leaves: Length: About 3.5 cm. Width: About 1.3 cm. Shape: Narrowly elliptic. Apex: Obtuse. Base: Attenuate. Margin: Nearly entire with occasional indentations. Apical leaves: Length: About 2.1 cm. Width: About 4.5 mm. Shape: Linear. Apex: Acute. Base: Attenuate. Margin: Entire. Texture, all leaves, upper and lower surfaces: Sparsely pubescent to glabrous. Color, all leaves: Developing foliage, upper surface: 147A. Developing foliage, lower surface: 147B. Fully developed foliage, upper surface: 147A to 147B; venation, 147A to 147B. Fully developed foliage, lower surface: 147B; venation, 147B.

Flower description:

*Flower type and habit.*—Flowers arranged singly at lateral apices. Flowers held mostly outwardly. Flowers persistent. Older flowers are overgrown by new flowers and foliage. Freely and continuously flowering. Flowers not fragrant.

*Flower shape.*—Tubular with three larger lower petals and two upright petals.

*Natural flowering season.*—Spring until frost in the autumn.

*Flower longevity on the plant.*—Longevity of individual flowers is highly dependent on weather conditions; typically three to ten days.

*Flower size.*—Diameter: About 2.1 cm. Tube length: About 7 mm. Throat diameter, distal end: About 4 mm. Tube diameter, proximal end: About 2 mm.

*Flower buds.*—Length: About 1 cm. Diameter: About 2 mm. Shape: Oblong. Color: 144C.

*Petals.*—Arrangement: Single whorl of five petals, fused; three larger lower petals and two smaller upper petals. Three lower petals: Shape: Broadly oblong. Length, above throat: About 1.2 cm. Width: About 7 mm. Two upper petals: Shape: Oblanceolate. Length, above throat: About 6 mm. Width: About 2 mm. Upper and lower petals: Apex: Cuspidate. Margin: Entire. Texture, upper and lower surfaces: Smooth, satiny. Color: When opening, upper surface: N81A. When opening, lower surface: 76B to 76C. Fully opened, upper surface: N82A to N82B; venation, similar as petal color. Fully opened, lower surface: 76C; venation, similar to petal color. Throat: 155C; spots, 79C; venation, 144A. Tube: 76C; venation, 144A.

*Sepals.*—Arrangement: Single whorl of five sepals, star-shaped calyx. Length: About 6.5 mm. Width: About 1.1 mm. Shape: Apiculate. Apex: Acute. Margin: Entire. Texture, upper and lower surfaces: Pubescent. Color, upper and lower surfaces: 147A.

*Peduncles.*—Appearance: Wiry, flexible. Length: About 2.2 cm. Diameter: About 0.7 mm. Texture: Sparsely pubescent to glabrous. Color: 147A.

*Reproductive organs.*—Stamens: Quantity per flower: About five, fused. Anther length: About 2.5 mm. Anther diameter: About 1.6 mm. Anther color: Between 77A and N92A. Pollen amount: Moderate. Pollen color: 9A. Pistils: Quantity per flower: One. Pistil length: About 9 mm. Stigma shape: Obovate. Stigma texture: Pubescent. Stigma color: N79A. Style length: About 5 mm. Style color: 146D. Ovary color: 147B. Seed/fruit: Seed and fruit production have not been observed.

Disease/pest resistance: Plants of the new *Lobelia* have not been noted to be resistant to pathogens and pests common to *Lobelia*.

Temperature tolerance: Plants of the new *Lobelia* have been observed to tolerate temperatures ranging from about 4° C. to about 30° C.

It is claimed:

1. A new and distinct cultivar of *Lobelia* plant named 'Wespinstar', as illustrated and described.

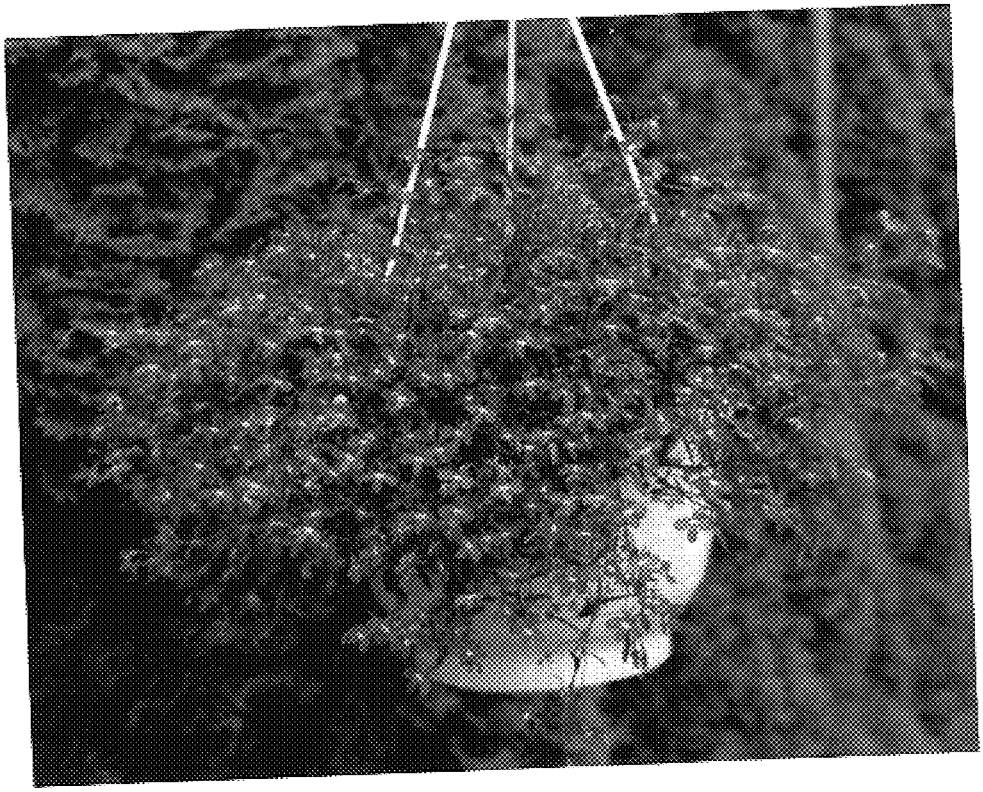
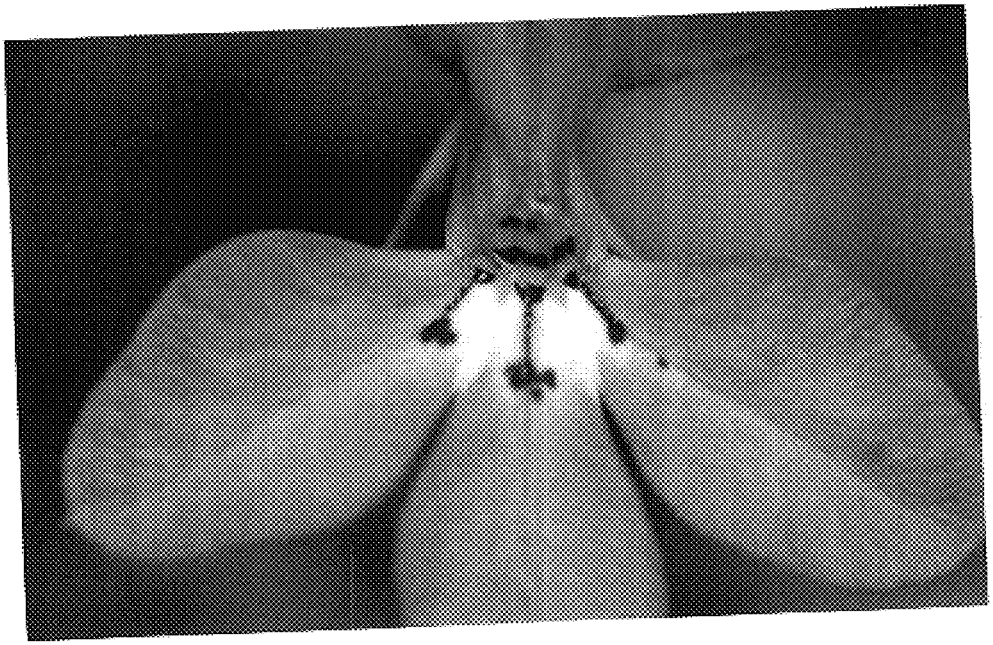

* * * * *